United States Patent [19]

Langer et al.

[11] 4,373,023

[45] Feb. 8, 1983

[54] PROCESS FOR NEUTRALIZING HEPARIN

[75] Inventors: Robert S. Langer, Cambridge; Robert Linhardt, Somerville; Charles L. Cooney, Brookline; Parrish M. Galliher, West Newton; Margaret M. Flanagan, Somerset, all of Mass.; Michael D. Klein, Ann Arbor, Mich.

[73] Assignee: Massachusetts Institute of Technology, Cambridge, Mass.

[21] Appl. No.: 196,720

[22] Filed: Oct. 14, 1980

[51] Int. Cl.³ .................. A01N 1/02; A61K 35/14
[52] U.S. Cl. .......................... 435/2; 424/94; 424/101
[58] Field of Search ............... 424/101, 94; 435/2

[56] References Cited

U.S. PATENT DOCUMENTS 3,766,167 10/1973 Lasker et al. ................ 424/180

OTHER PUBLICATIONS

Cho et al.–Chem. Abst., vol. 50 (1956), p. 14023a.
Jaques–J. Biol. Chem., vol. 133 (1940), pp. 445–451.

*Primary Examiner*—Sam Rosen
*Attorney, Agent, or Firm*—Arthur A. Smith, Jr.; Paul J. Cook

[57] ABSTRACT

Blood containing heparin and treated extracorporeally is contacted with immobilized heparinase prior to being reintroduced into the patient.

5 Claims, 1 Drawing Figure

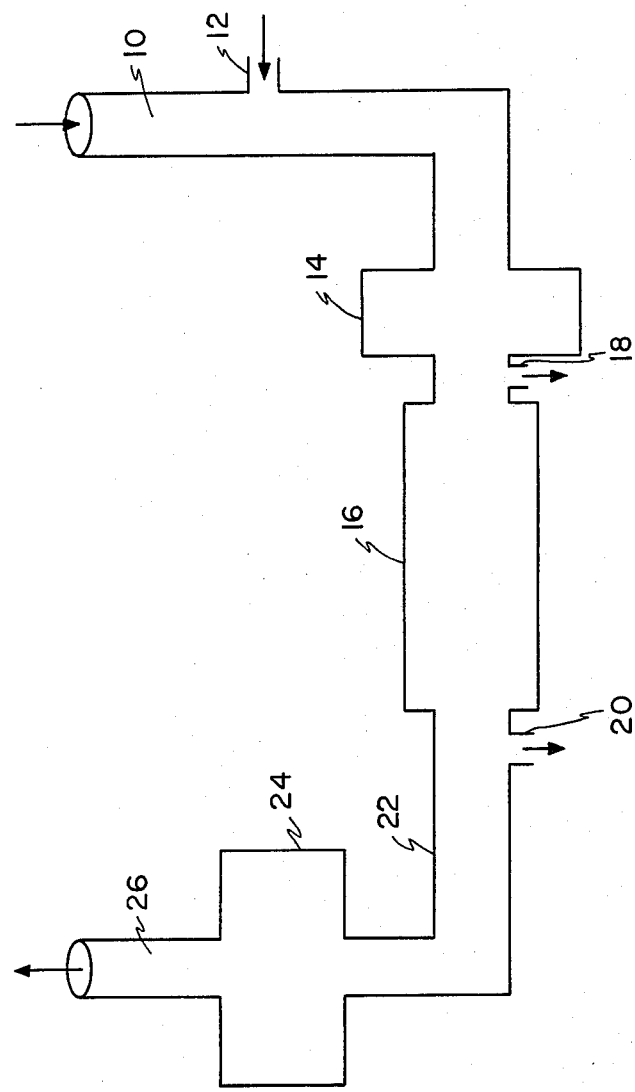

PROCESS FOR NEUTRALIZING HEPARIN

The Government has rights in this invention pursuant to Grant Number NIH-5-RO1-GM25810-02 awarded by the U.S. Department of Health and Human Services.

BACKGROUND OF THE INVENTION

This invention relates to a process and composition for neutralizing heparin and more particularly to a process and composition for neutralizing heparin administered to a patient.

Heparin is a mucopolysaccharide composed mainly of alternating structures of D-glucosamine and L-iduronic acid with a molecular weight ranging between 8000 and 15,000 daltons. It has a strong negative charge. The blood anticoagulating effect of heparin is believed due to blocking the elaboration of prothrombin or inhibiting, in the presence of a plasma cofactor, the action of thrombin and the conversion of fibrinogen to fibrin.

Heparin has found numerous applications in the area of hemodialysis pulmonary embolism disseminated intravascular coagulation, peripheral vascular surgery, cardiac surgery, transplantation and autotransfusion. Extracorporeal medical devices, e.g., artificial kidney, pump-oxygenator, profused with blood have been an effective part of therapy for many years. These devices all rely on systemic heparinization to provide the blood compatibility. Despite continuous efforts to improve anticoagulation techniques, many patients still develop coagulation abnormalities with the use of these devices. Devices such as the membrane oxygenator which utilize even longer profusion times, the drawbacks of systemic heparinization are multiplied. A number of approaches have been attempted to solve this problem. These include: administration of compounds, development of heparin substitutes, bonding heparin or other substances to the extracoporeal device and development of new blood-compatible material for construction of the extracorporeal device. Although the approach has led to some improvements, control of blood heparin levels remains a serious problem. Heparin usage has permitted control of coagulation and prevention of active clotting but can cause severe complications. The most frequent complication of heparin therapy is hemorrhage. The severity of the hemorrhage may vary from mild mucosal oozing to massive intracranial, gastrointestinal and intrathoracic bleeding. The incidence of hemorrhage resulting from heparization is about 8-33%. Coagulation abnormalities have increated drastically with the recent developments of long-term pulmonary support with membrane oxygenators. In addition to hemorrhage, there are a number of other complications associated with heparinization, particularly when the drug is administered over a long period. Some of these complications include alopecia, interference with bone repair, leading in some cases, to severe decalcifying bone disease.

Because of the complications associated with heparin therapy, the need exists to neutralize heparin, thereby destroying its anti-coagulant activity. The primary treatment utilized in the neutralization of heparin has been combining it with a positively charged drug. The clinical choice for this purpose has been protamine sulfate. The administration of protamine to neutralize heparin, however, may produce hypotension and also can produce a rise in pulmonary artery pressure, a fall in lung compliance and a reduction in arterial oxygen tension.

Complications associated with heparin therapy and its neutralization have caused considerable attention to be focused on devising means for permitting extracorporeal blood flow without heparinization. One approach is to utilize heparin substitutes. However, heparin is still the anti-coagulant suitable for routine use in extracorporeal circuits. A major effort has been made to develop new extracorporeal surfaces or methods of coating commonly used surfaces with heparin or other additives. The most common of these approaches has been the binding of heparin itself to the extracorporeal surface by means of covalent bonding or by a non-specific means such as ionic bond. Another approach is to include the binding of hydro gels, chemical attachment of urokinase, the use of negatively charged materials, new bio-materials and coating with substances such as silicone. In spite of these efforts, it seems clear that heparinization will continue to be important; because of the complications that heparin can cause, it would be desirable to have an effective means for controlling its concentration.

SUMMARY OF THE INVENTION

The present invention is based upon the use of immobilized heparinase to degrade heparin in the blood in an extracorporeal device prior to recirculating the blood to the patient. The blood is drawn from the patient in order to be directed to an extracorporeal device such as a blood oxygenator, kidney dialysis apparatus or the like in the usual manner. Heparin is added to the blood in the usual manner in order to minimize or prevent blood coagulation. After the blood has been treated in the desired manner, it is contacted with the immobilized heparinase in accordance with this invention in order to degrade substantially all or all of the heparin in the blood prior to being re-introduced into the patient. In this manner, the patient is exposed to neither heparin or heparinase. Thus, this invention provides substantial advantages with respect to patients' safety as compared to prior art methods for controlling coagulation.

BRIEF DESCRIPTION OF THE DRAWING

The FIGURE is a schematic drawing illustrating the apparatus of this invention.

DESCRIPTION OF SPECIFIC EMBODIMENTS

In accordance with this invention, heparinase is immobilized on a polymeric support so that it can be contacted with blood containing heparin to remove the heparin from the blood. The polymer or gel support comprises a material which does not interact with the blood in a toxic manner. Representative suitable supports include cross-linked dextran (Sepharose), polyacrylamide, polyhema.

The particular method for immobilizing heparinase will depend upon the support utilized. For example, immobilization on Sepharose is accomplished by reacting Sepharose which has been activated with cyanogen-bromide such as by the following representative procedure: To 1 mL of swelled beads and 1 mL of water 2 mL of 2 M $Na_2CO_3$ was added after mixing 0.1 mL of Acetonitrile containing 200 mg of Cyanogen Bromide was added and the mixture was stirred rapidly for 1 to 2 min. The resulting activated beads were then washed with 20 mL of 0.1 M $NaHCO_3$ (pH 9.5) 20 mL of water, 20 mL of 0.07 M Sodium Phosphate 0.125 M Sodium Chloride at pH 7.0 and then these activated beads were used immediately. This activation was best performed at 4° C. but also worked when performed at 20° C. The modified Sepharose then is contacted with heparinase in aqueous solution under conditions to effect bonding of the heparinase to the Sepharose through the activated linkage. Generally, the heparinase is in solution at concentrations of generally about 0.1 mg/mL–5 mg/mL preferably about 0.5 mg/mL. The pH of the solution is maintained between about 6 and about 10, preferably between about 7 and about 7.5, while the temperature during the action is maintained about 1° C. and about 10° C., preferably between about 4° C. and about 5° C. Substantially complete coupling of the heparinase to the Sepharose substrate generally occurs within about 24 hours. Immobilization on polyhema (poly hydroxylethyl methacrylate) uses the same procedure as Sepharose CNBr.

In the case of polyacrylamide, the substrate is first activated with an active ester such as N-hydroxy succinamide. Heparinase then is added to the modified polyacrylamide to effect heparinase coupling through the coupling group. Generally, this reaction is substantially complete within about 1 hour. The immobilized enzyme then can be stored with or without heparin at a pH of between about 4 and about 10, at a temperature between about 4° C. and 37° C.

Methods for immobilized heparinase on the support include the following: coupling to an aldehyde, triazine, or acylazide activated support.

The source of the heparinase utilized in the present invention is not critical. Thus, for example, the heparinase can be obtained from other microbial sources, human platelets or human placenta. A particularly preferred source of the heparinase is disclosed in a co-pending application filed concurrently herewith entitled, "Process for Producing Heparinase", Cooney et al. As disclosed in the co-pending application, heparinase is produced from *Flavobacterium heparinum* such as *Flavobacterium heparinum* ATCC 13125 or other mutant strains. Cell growth and increased heparinase activity is attained by utilizing a chemically defined growth medium comprised of a carbon source, a nitrogen source, a phosphate source, a magnesium source and a heparinase inducer, two amino acids and trace salts in the absence of protein digest or yeast extract. The carbon source utilized can be comprised of glucose, maltose, glycerol or heparin.

The nitrogen source can comprise ammonium sulfate, ammonium chloride, ammonium phosphate, heparin or amino acids. The phosphate source can comprise potassium mono or di basic phosphate or sodium mono or di basic phosphate or ammonium phosphate or mixtures thereof. The magnesium can comprise magnesium sulfate, magnesium chloride or magnesium phosphate. The heparinase inducer can comprise heparin, in salt form such as sodium salt, hyaluronic acid, maltose, heparin monosulfate or N-acetyl D-glucosamine. In this process, it has been found that the absence of a protein digest or yeast extract results in materially increased rates of production of heparinase and a material increase in the total activity of the heparinase recovered. Fermentation is conducted at a temperature between about 22° C. and about 25° C. The initial concentration of the carbon source is between about 5 g/L and about 10 g/L, while the initial concentration of the nitrogen source is between about 1 g/L and about 2 g/L. The initial concentration of the phosphate source is between about 3 g/L and about 5 g/L, while the initial concentration of the magnesium source is between about 0.5 g/L and about 1 gm/L. The initial concentration of the heparinase inducer is between about 0.15 g/L and about 10 g/L. L histidine and L methionine between 0.2–0.5 g/L and trace salts at $1 \times 10^{-5}$–$1 \times 10^{-5}$ M. It is also possible to conduct this process on a continuous basis by limiting one required nutrient. By utilizing this process, an increase in heparinase productivity of about 3 orders of magnitude over prior processes can be attained and the heparinase productivity of the heparinase can be increased by about 3 orders of magnitude over the best known prior art processes. It is also desirable in this process to control pH between about 6 and about 8, dissolved oxygen between about 0 and about 100% of air saturation and to maintain agitation during fermentation.

The apparatus of this invention comprises the combination of any conventional apparatus for treating blood in the presence of heparin, a chamber containing immobilized heparinase and means for passing the blood through the blood treatment device and subsequently through the chamber containing the immobilized heparinase. Representative suitable devices for treating blood in accordance with this invention include blood oxygenators wherein blood and oxygen and passed on opposing surfaces of a membrane through which oxygen and carbon dioxide can diffuse, a kidney dialysis device wherein blood and isotonic buffer are passed on opposing sides of a membrane through which urea and other toxic catabolites can diffuse. In these devices, blood is withdrawn from a patient through a catheter or the like and heparin is introduced into the blood in order to substantially prevent blood coagulation. The resultant mixture of blood and heparin is pumped into a blood treating device wherein the desired blood treatment is effected. Thereafter, the blood and heparin are contacted with the immobilized heparinase in order to deactivate the heparin so that it does not cause bleeding in the patient when the blood is returned to the patient. The amount of heparinase immobilized on the polymer or gel is sufficient to substantially completely deactivate the heparin in the blood. The thus-treated blood then is returned to the patient.

Referring to the FIGURE, blood is drawn from a patient through a catheter (not shown) and into conduit 10. Heparin is introduced into conduit 10 through conduit 12 and the resultant mixture is drawn by means of pump 14 into blood oxygenator 16 wherein carbon dioxide in the blood is exchanged for oxygen. The apparatus can be provided with sampling ports 18 and 20 in order to monitor the efficiency of the oxygenator 16. The oxygenated blood containing heparin is passed through conduit 22 into chamber 24 which contains one or a plurality of membranes in the form of flat sheets, cylindrical channels, beads or the like through which the blood and heparin is passed in order to deactivate the heparin substantially completely. The deheparinized blood is removed from chamber 24 through conduit 26 and is returned to the patient through a catheter (not shown).

The following examples illustrate the present invention and are not intended to limit the same.

EXAMPLE I

This example illustrates a method for immobilizing heparinase. Sepharose 4B activated with cyanogenbromide was obtained from Pharmacia Fine Chemical Co.

under the trade name CNBr Activated Sepharose 4B. Sepharose 4B, comprised of cross-linked dextran, is activated with cyanobromide to the extent of being able to bind from 5-10 mg Protein/mL swelled gel.

Heparinase (5 cc in 0.07 M sodium phosphate and 0.125 M sodium chloride at pH 7.0) obtained by the process of Example II was admixed with 1 gm of swelled CNBr activated Sepharose 4B in a 0.07 M sodium phosphate and 0.125 M sodium chloride (pH 7.0) solution at a concentration of between about 0.1 mg/mL and about 1.0 mg/mL protein and shaken at 4° C. (between 1° and 10° C.) for 16 h (between 8 and 24 h) also the addition of 60 mg of sodium heparin increased the activity of the immobilized heparinase product. After about 16 hours, the extent of heparinase immobilization on the Sepharose was determined by measuring the residual protein in the buffer after 90% of the protein was immobilized the reaction was stopped. Thereafter, the Sepharose containing the immobilized heparinase was treated as follows: Washed with the above phosphate buffer and was stirred with 20 cc of 0.2 M glycine pH 8.3 to block excess active groups. The beads were again washed with the same phosphate buffer as above at pH 7.0 and were stored in this buffer at 4° C.

The immobilized enzyme retains approximately 13% of its activity after immobilization and becomes substantially more stable retaining essentially all of its activity after one month's storage at 4° C. as compared to the free enzyme which loses approximately one half of its activity after one week at 4° C.

EXAMPLE II

This example illustrates a preferred method for producing heparinase which can be immobilized in accordance with this invention.

*Flavobacterium heparinum* ATCC 13125 was mixed with a chemically defined growth medium comprising glucose, 10 g/L as the carbon source, 2 g/L as the nitrogen source, 5 g/L as the phosphate source, 0.5 g/L as a magnesium source and 1.0 g/L as the heparinase inducer L-histidine and L-methionine 0.5 g/L and trace salts $1 \times 10^{-4}$ M. After about 25 hours, the cells were harvested after growth, sonicated and heparinase activity was assayed. Heparinase was recovered by hydroxylapatite purification.

EXAMPLE III

This example illustrates the process of this invention showing heparinase activity for deactivating heparin.

A sample (3 cc) of fresh rabbit blood was drawn over heparin (0.02 g/L) and was split into 3 tubes each containing 1 cc heparinized whole blood. Crude heparinase (1 mg) then was added to one tube. Heat deactivated (45° C. for 15 minutes) crude heparinase (1 mg) was added to a second tube (Control A). No heparinase was added to the third tube (Control B). Each tube was shaken and the clotting time for each tube was measured as follows:

|  | Clotting Time, Minutes |
|---|---|
| Tube 1 | 9 |
| Tube 2 (Control A) | 20 |
| Tube 3 (Control B) | 19 |

Thus, it is apparent that heparinase reduced the heparin activity by 50%.

We claim:

1. In the process for treating the blood of a patient extracorporeally wherein heparin is introduced into the blood to substantially prevent blood coagulation, the improvement which comprises passing said treated blood containing heparin into contact with an immobilized heparinase, said heparinase being derived from *Flavobacterium heparinum*, in order to deactivate said heparin prior to reintroducing said treated blood into the patient.

2. The process of claim 1 wherein the immobilized heparinase is bound to a substrate comprising cross-linked dextran.

3. The process of any one of claims 1 or 2 wherein the blood is treated to remove carbon dioxide and to introduce oxygen thereto.

4. The process of any one of claims 1 or 2 wherein said blood is treated to remove urea.

5. The process of claim 1 or 2 wherein said heparinase is derived from *Flavobacterium heparinum* ATCC 13125.

* * * * *